(12) United States Patent
Hoernig

(10) Patent No.: US 8,451,973 B2
(45) Date of Patent: May 28, 2013

(54) DEVICE AND METHOD FOR MAMMOGRAPHY

(75) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 207 days.

(21) Appl. No.: 12/897,036

(22) Filed: Oct. 4, 2010

(65) Prior Publication Data

US 2011/0129062 A1    Jun. 2, 2011

(30) Foreign Application Priority Data

Nov. 27, 2009  (DE) .......................... 10 2009 056 176

(51) Int. Cl.
*A61B 6/04*    (2006.01)
*A61B 6/00*    (2006.01)

(52) U.S. Cl.
CPC ..................................... *A61B 6/502* (2013.01)
USPC ............................................. 378/37; 378/195

(58) Field of Classification Search
USPC ............................................ 378/37, 195, 208
See application file for complete search history.

(56) References Cited

U.S. PATENT DOCUMENTS 4,691,333 A      9/1987  Gabriele et al.
2007/0280412 A1*  12/2007  Defreitas et al. ................ 378/37

* cited by examiner

*Primary Examiner* — Hoon Song
(74) *Attorney, Agent, or Firm* — Schiff Hardin LLP

(57) ABSTRACT

A compression unit of a mammography apparatus includes an arrangement to tension at least one compression band in a first fixing unit and second fixing unit arranged on both sides of a subject table.

10 Claims, 3 Drawing Sheets

DEVICE AND METHOD FOR MAMMOGRAPHY

BACKGROUND OF THE INVENTION

1. Field of the Invention

The invention concerns a device and a method for mammography, in particular a compression unit of a mammography apparatus to compress the breast during a mammography acquisition or a biopsy extraction.

2. Description of the Prior Art

A mammography system is essentially formed from an x-ray arm arranged such that it can pivot on a stand, the x-ray arm has an x-ray source and a detector unit. The surface of the detector unit is designed as a support surface for a breast of a patient that is to be examined. The x-ray arm and the detector unit can be formed such that these can be moved independently of one another. To better detect malignant tissue in an x-ray exposure, the breast to be examined is pressed onto the support surface or, fixed thereon by means of a compression unit. The compression plate of the compression unit is moved horizontally for this purpose. However, the use of a compression plate has the disadvantage that a central support of the breast on the subject table should preferably be sought. This often can be achieved only with increased stress (exertion) for the patient and the operator.

SUMMARY OF THE INVENTION

An object of the invention is to provide an improved compression unit.

In the device and associated method according to the invention, a subject table is designed such that at least one compression band connecting a first fixing unit and a second fixing unit is provided, a tensioning arrangement that tensions the compression band is arranged in the first and second fixing unit. The adjustable tension force of the compression bands is monitored with sensor units The compression of the breast can ensue with convex symmetry by means of connecting bars arranged at the subject table.

The invention has the advantage that the breast can be positioned at an arbitrary point of the bearing surface or, respectively, the subject table which allows the greatest degree of patient comfort.

The invention also has the advantage that an asymmetrical compression is enabled depending on the application without modifying the compression unit.

The invention also has the advantage that the individual requirements of the patient can be addressed with a simple, flexible adjustment.

The invention has the further advantage that a subsequent alignment of the breast on the subject table can be omitted.

The invention also has the advantage that a mechanical structure at the mammography system is omitted.

The invention has the additional advantage that mechanical pressing units of different design are necessary.

DESCRIPTION OF THE PREFERRED EMBODIMENTS

Figure 1:
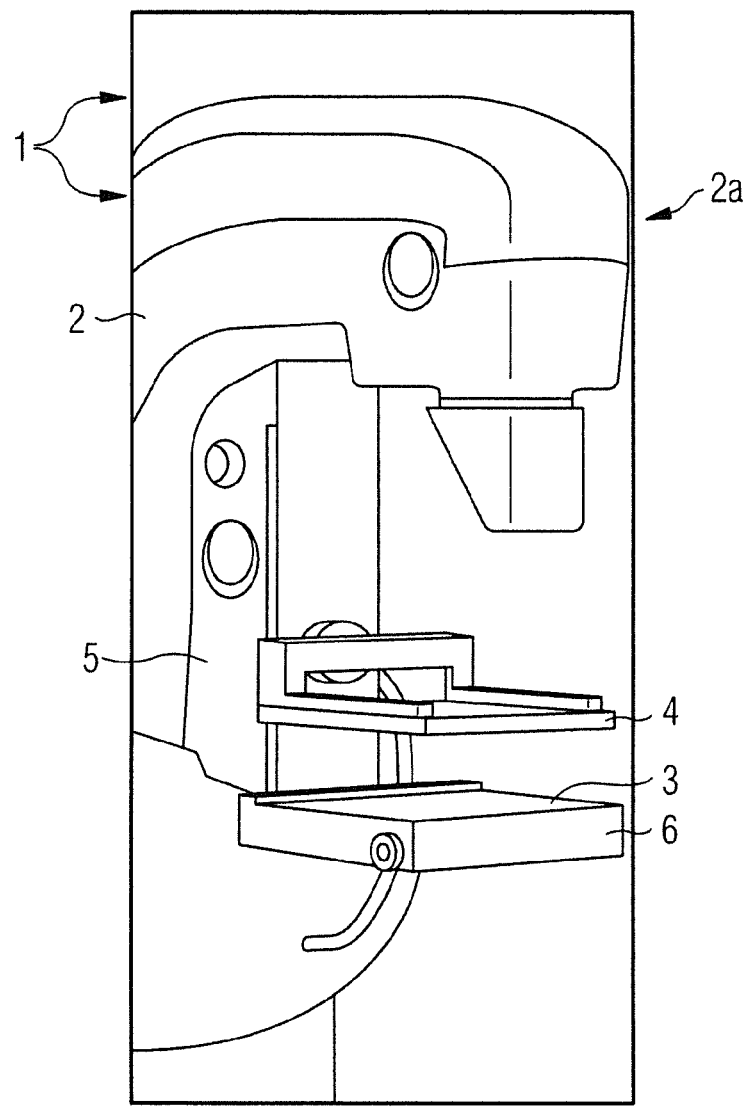
FIG. 1 shows a conventional arrangement (design) of an x-ray arm with a compression unit above a subject table.

FIG. 1 shows a section of a conventional mammography apparatus. This part of the mammography apparatus shows an x-ray arm 2 with x-ray head 2a as well as a detector 6 arranged opposite this. The top side of the detector 6 is used as a subject table 3. An adjustment device for a compression plate 5 is arranged set back in the extension of the plane of the subject table 3. The adjustment device 5 and the compression plate 4 are designated as a compression unit. The compression plate 4 can be lowered or raised horizontally by a motor by means of the electronic control unit integrated into the adjustment device 5.

Figure 2:
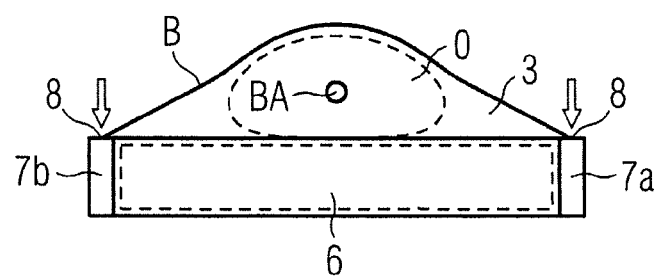
FIG. 2 is a front view of a subject table with an additional compression unit in accordance with the invention.

FIG. 2 shows a front view of a subject table 3 with a detector unit 6 integrated into this. As shown at the bottom of FIG. 1, the subject table 3 is arranged opposite an x-ray source. A first fixing unit 7a and a second fixing unit 7b are arranged on both sides of the subject table 3. Motorized, controllable tension devices for a compression band B are respectively integrated into these fixing units 7a, 7b. A breast to be examined—which is also designated as subject O in the following—is positioned below the compression band B on the subject table and compressed or fixed on the subject table 3 by means of the compression band B before a scan or an x-ray acquisition. The first fixing unit 7a is arranged on the right side of the subject table 3 and the fixing unit 7b is arranged on the left side. The depth of the first and second fixing unit 7a, 7b can extend over the entire depth of the subject table 3 or, respectively, the detector 6, corresponding to that of the subject table 3. The first and second fixing units are of symmetrical design. The compression arrangement shown in FIG. 2 and the following figures is designated as a compression band B or flexible band. The compression band B, B1, B2 is transparent to radiation. The material from which the compression band B, B1, B2, . . . is formed can be, for example, polyester-spandex or polyamide. The compression band B is wound or unwound on a cylinder at both sides in the first and second fixing units 7a, 7b of the subject table 3, according to the requirements of the examination. For this purpose, the cylinder can be driven with an electromotor so that the compression band is wound or unwound. A more detailed embodiment of the first and second fixing unit 7a, 7b is described in FIGS. 4 and 5. The adjustable tension force of the compression band B is monitored by means of sensors, for example strain gauges. The right-side and left-side fixing units 7a, 7b can be controlled such that different pulling forces can be applied to the ends of the compression band B. The respective adjustable pulling or tensioning forces for the compression bands B, B1, B2, . . . can be individually provided on a patient-by-patient basis in the first and second fixing units 7a, 7b. The compression force selected for a patient can be stored in a control unit (not shown) or be recorded in a patient file. This data can then be accessed given a new examination.

Figure 3:
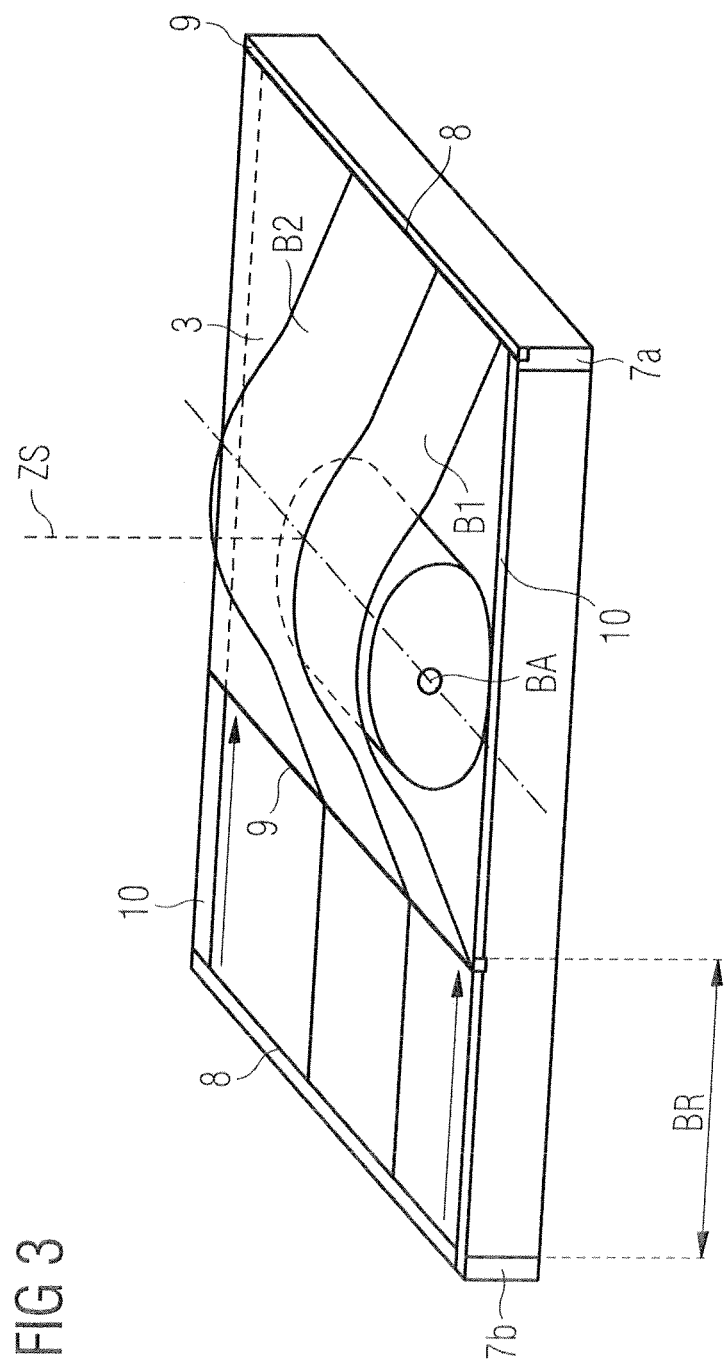
FIG. 3 is a perspective representation of the subject table with a compression unit in accordance with the invention.

The subject table 3 with the first and second fixing units 7a, 7b that is used in a mammography apparatus is depicted in FIG. 3. The embodiment explained in the following enables an asymmetrical support and compression of the breast on the subject table. FIG. 3 depicts a perspective representation of the subject table 3 with the first and second fixing unit 7a, 7b.

Guide rails 10 are arranged on the top side of the front side and back side of the subject table 3. Both guide rails 10 are connected with one another via at least one connecting rod 9. This connecting rod 9 is fashioned so that it can be displaced so that the compression field can be individually distributable by means of the connecting rod 9. If, due to individual characteristics, the patient is positioned to the right side of the subject table 3 and the breast is likewise positioned to the right side of the subject table, the connecting rod 9 can be displaced along the guide rails 10 at both sides of the breast and relative to said breast in order to achieve (for example) a symmetrical curve of the compression band B relative to the breast. This connecting bar 9 has the advantage that the compression band extends with convex symmetry over the breast. The compression band B rolled up in the first and second fixing units 7a, 7b respectively extends from the first fixing unit 7a over a guide edge 8 to the second fixing unit 7b. The compression band B extends from the first or second fixing unit 7a or 7b to the respective opposite fixing unit 7b or 7a. If the subject O now rests to the right side on the subject table 3, the compression unit thus can be adapted relative to the position and size of the subject O. In the shown depiction the compression band B is subdivided into two compression bands B1, B2, for example. The compression bands B1, B2 lie flat on the left part of the subject table 3 between connecting rod 9 and guide edge 8. With the lateral positioning of the connecting rod 9, its translation or, respectively, displacement BR is communicated to the diaphragm controller (not shown here) of the x-ray head 2a. If the right-side connecting rod 9 is additionally displaced towards the breast positioned on the subject table 3, the lateral translation BR of the connecting rod 9 that is produced there is likewise communicated to the diaphragm controller of the x-ray head 2a. Both possible displacements of the connecting rods 9 produce an electronic adjustment of the diaphragms of the x-ray head 2a, such that a central x-ray beam ZS of an x-ray beam emitted by the x-ray head 2a strikes the imaginary subject/breast axis BA. An additional embodiment of the shown fixing unit 7a, 7b is designed such that the compression bands B, B1, B2, can, for example, exhibit a slightly different elasticity and can be wound with different compactness on the cylinders AW arranged in the first and second fixing unit 7a, 7b. For example, compression bands B, B1, B2 with slightly different or partial elasticity can also be used for the examination of a breast. In addition to this, compression bands which are less flexible at the breast wall or, respectively, more elastic further from the breast wall can be used as compression bands. The lateral edges of the compression bands are arranged relative to one another so that no compression-free stripes or surfaces form at the contact point. For this the compression bands B1, B2, . . . adjoining one another could be connected with an elastic material. If the compression of the breast ends again after a scan or an individual exposure, an arresting of the winding/unwinding rollers Aw is canceled, for example. The compression bands B, B1, B2, . . . can be used with at least one opening for the extraction of a biopsy. The biopsy needle can then be placed within an opening in the band B, B1, B2, . . . corresponding to the locality of the altered tissue structure, and a tissue sample can be extracted for a histological examination.

Figure 4:
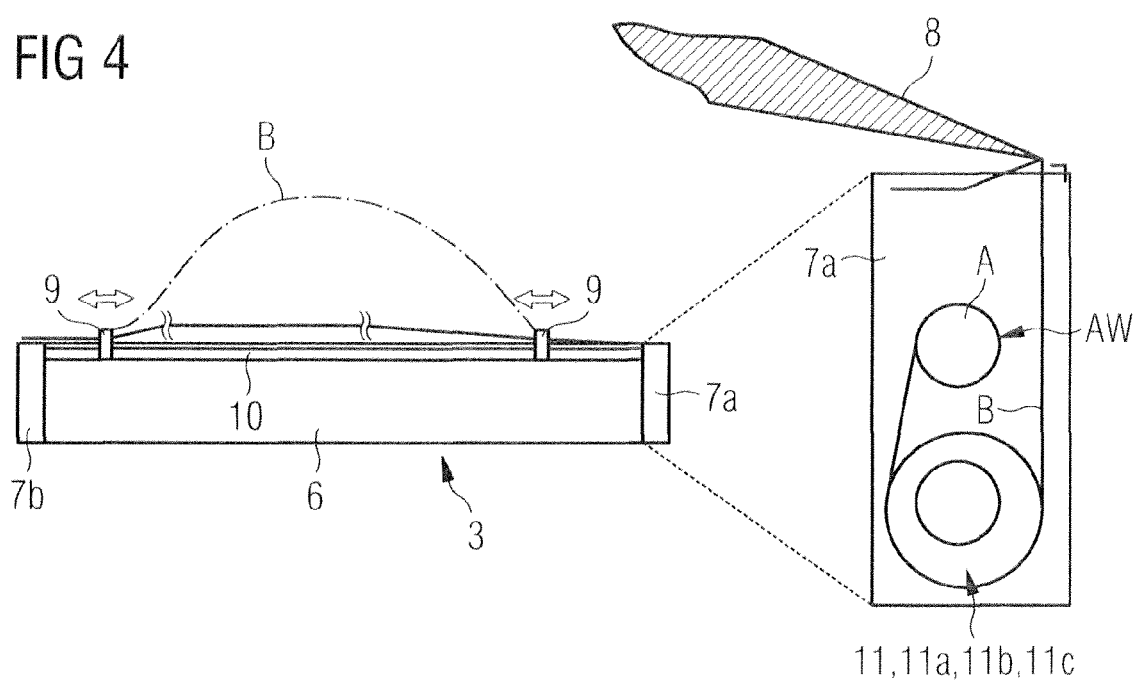
FIG. 4 is an additional front view of a compression unit with a detail view of a compression unit in accordance with the invention.

A front view of the subject table 3 with the detector 6 integrated into this is schematically depicted in FIG. 4. The first and second fixing units 7a, 7b are arranged to the sides of the subject table 3. Likewise shown are the connecting rods 9 that can be arranged so as to be displaceable in the guide rails 10. The compression band B then respectively runs between the fixing units 7a, 7b and the connecting rod 9, parallel to the surface of the subject table 3. The compression band is compressed between the two connecting rods 9 so as to be convex, such that sufficient space for a subject to be examined forms between compression band and surface of the subject table 3. The first fixing unit 7a is shown in cross section as an example. A cylinder AM (that, driven by a motorized axle, can be operated as a winding/unwinding roller) and a deflection roller 11 are integrated into the fixing unit. The compression belt B arrives via the guide edge 8 in the fixing unit, wherein the compression band is rolled up or rolled out on the motorized winding or unwinding roller via a deflection roller 11. If multiple compression bands B1, B2, . . . are used, the motorized cylinder AW is decoupled corresponding to the width and number of bands, meaning that ever compression band B1, B2, . . . can be rolled up or rolled out separately with a variable tension force. The number of deflection rollers 11, 11a, 11b, 11c, . . . in the fixing units 7a, 7b is adapted corresponding to the number of compression bands B1, B2, . . . Sensor units and adjustment means that respectively, individually (corresponding to the respective compression band) measure the tension force relative to the compensation band and/or can adjust the tension force of the compression band via the adjustment means are arranged on each axle of the deflection rollers. A measurable or adjustable torque can likewise be predetermined for the motorized drive. Memory units can be provided in a control unit or in the adjustment means to store adjustment values individual to the patient.

Figure 5:
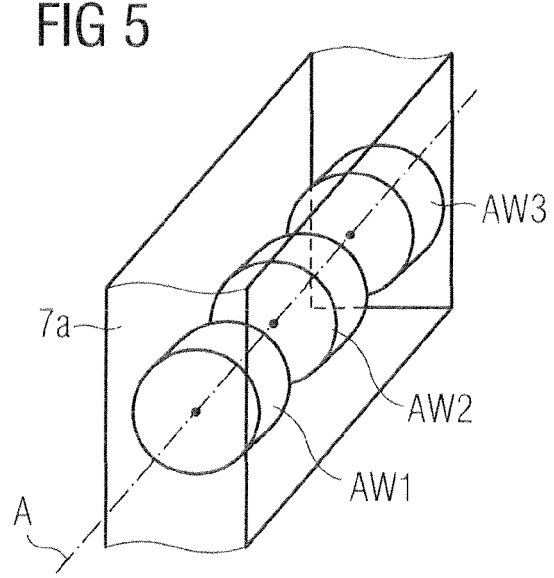
FIG. 5 is a perspective representation of an additional detail view of a compression unit in accordance with the invention.

The fixing unit 7a is shown in a perspective depiction as an example in FIG. 5. In this depiction the distribution of the cylinder AW (already mentioned with regard to FIG. 4) is shown in an embodiment of the fixing unit with 3 compression bands, for example. A first, a second and a third cylinder AW1, AW2, AW3 are arranged along an axis A. The drive of the first, second and third cylinder AW1, AW2, AW3 is fashioned so as to be decoupled. The actuation of the cylinder AW1, AW2, AW3 can ensue by means of one or more electromotors. The torque at every individual cylinder can be predeterminably, individually adjusted and electronically monitored by means of sensor units by means of the separately controllable first, second and third cylinders AW1, AW2, AW3. This has the advantage that an optimized, individual (customized) compression of the breast is possible.

Although modifications and changes may be suggested by those skilled in the art, it is the intention of the inventor to embody within the patent warranted hereon all changes and modifications as reasonably and properly come within the scope of his contribution to the art.

I claim as my invention:

1. A mammography device comprising:
   a subject table adapted to support a female breast at an arbitrary location thereon;
   a first fixing unit and a second fixing unit attached to said subject table and integrated as parts of said subject table;
   a compression band extending between and connected to said first and second fixing units, said compression band spanning at least a portion of said subject table in a spanning direction;
   said first and second fixing units comprising a tensioning arrangement configured to tighten said compression band without detachment of said compression band from said support table, to compress a female breast supported on said subject table; and
   at least one of said first and second fixing units comprising a rod mounted on said support table for horizontal displacement along said spanning direction to lengthen or shorten a portion of said compression band in contact with a female breast on said support table to centrally apply a compression force to the female breast.

2. A mammography device as claimed in claim 1 wherein said tensioning arrangement comprises a tension adjuster that adjusts a tension force of said compression band, and at least one sensor unit that detects said tension force.

3. A mammography device as claimed in claim 1 comprising guide rods mounted at said support table and proceeding substantially parallel to said spanning direction, and connecting said rod to said guide rods as a connecting rod that is slideable along said guide rods.

4. A mammography device as claimed in claim 1 comprising an x-ray source located opposite to said subject table and it being mounted with respect to said subject table to allow alignment of said x-ray source with the breast on the support table dependent on a position of said connecting rod.

5. A mammography device as claimed in claim 1 comprising a radiation detector located beneath said subject table.

6. A mammography method comprising the steps of:
supporting a female breast on a subject table at an arbitrary location thereon;
providing a first fixing unit and a second fixing unit as integrated parts of said subject table, and providing at least one of said first and second fixing units with a rod;
extending a compression band between and connected to said first and second fixing units and, with said compression band, spanning at least a portion of said subject table in a spanning direction;
operating said first and second fixing units as a tensioning arrangement to tighten said compression band without detachment of said compression band from said support table, to compress a female breast supported on said subject table by horizontally displacing said rod on said support table along said spanning direction to lengthen or shorten a portion of said compression band in contact with a female breast on said support table to centrally apply a compression force to the female breast.

7. A mammography method as claimed in claim 6 comprising forming said tensioning arrangement as a tension adjuster that adjusts a tension force of said compression band and, with at least one sensor unit, detecting said tension force.

8. A mammography method as claimed in claim 6 comprising mounting guide rods at said support table and proceeding substantially parallel to said spanning direction, connecting said rod between said guide rods as a connecting rod, and sliding said connecting rod along said guide rods.

9. A mammography method as claimed in claim 6 comprising mounting an x-ray source opposite to said subject table and aligning said x-ray source with the breast on the support table dependent on a position of said connecting rod.

10. A mammography method as claimed in claim 6 comprising irradiating the breast with radiation and detecting radiation attenuated by the breast with a radiation detector located beneath said subject table.

* * * * *